(12) United States Patent
Ban et al.

(10) Patent No.: US 11,051,721 B2
(45) Date of Patent: Jul. 6, 2021

(54) SYSTEM, METHOD, AND PROGRAM FOR INITIALIZING ATTACHMENT LOCATION OF MEASUREMENT SENSOR

(71) Applicant: NEOFECT Co., Ltd., Seongnam-si (KR)

(72) Inventors: Hoyoung Ban, Yongin-si (KR); Younggeun Choi, Yongin-si (KR); Soobin Lee, Seongnam-si (KR)

(73) Assignee: NEOFECT Co., Ltd., Seongnam-si (KR)

( * ) Notice: Subject to any disclaimer, the term of this patent is extended or adjusted under 35 U.S.C. 154(b) by 108 days.

(21) Appl. No.: 16/395,091

(22) Filed: Apr. 25, 2019

(65) Prior Publication Data

US 2019/0246956 A1    Aug. 15, 2019

Related U.S. Application Data

(63) Continuation of application No. 15/344,601, filed on Nov. 7, 2016, now Pat. No. 10,314,522, which is a
(Continued)

(51) Int. Cl.
*A61B 5/11* (2006.01)
*A61B 5/00* (2006.01)
(Continued)

(52) U.S. Cl.
CPC ............ *A61B 5/1126* (2013.01); *A61B 5/002* (2013.01); *A61B 5/1114* (2013.01);
(Continued)

(58) Field of Classification Search
CPC ... A61B 5/1126; A61B 5/1121; A61B 5/1123; A61B 5/002; A61B 5/1114; A61B 2503/10; G06F 19/30
(Continued)

(56) References Cited

U.S. PATENT DOCUMENTS

| 9,320,957 | B2 | 4/2016 | Bentley |
| 2013/0128022 | A1 | 5/2013 | Bose et al. |
| 2015/0109006 | A1 | 4/2015 | Choi et al. |

FOREIGN PATENT DOCUMENTS

| JP | 2004-184351 A | 7/2004 |
| KR | 10-2010-0050613 A | 5/2010 |
| KR | 10-2010-0068770 A | 6/2010 |
| KR | 10-2012-0000807 A | 1/2012 |

(Continued)

OTHER PUBLICATIONS

The extended European search report issued by the European Patent Office dated Feb. 5, 2019, which corresponds to European Patent Application No. 15891029.9 and is related to U.S. Appl. No. 15/344,601.

(Continued)

*Primary Examiner* — Robert R Raevis
(74) *Attorney, Agent, or Firm* — Studebaker & Brackett PC

(57) ABSTRACT

Disclosed are a system, a method, and a program for initializing an attachment location of a measurement sensor. The method of determining an initial attachment location of at least one measurement sensor includes at least: retrieving, by the terminal, identification information of the at least one measurement sensor selected from a user, as the terminal receives a selection input for the at least one measurement sensor attached to a particular location of a body of the user, from the user; and matching, by the terminal, the retrieved identification information with the particular location of the body where the at least one measurement sensor is configured to be attached such that the initial attachment location of the at least one measurement sensor is determined.

13 Claims, 3 Drawing Sheets

Related U.S. Application Data continuation of application No. PCT/KR2015/010698, filed on Oct. 12, 2015.

(51) Int. Cl.
  *G16H 40/63* (2018.01)
  *G16H 20/30* (2018.01)

(52) U.S. Cl.
  CPC .......... *A61B 5/1121* (2013.01); *A61B 5/1123* (2013.01); *G16H 20/30* (2018.01); *G16H 40/63* (2018.01); *A61B 2503/10* (2013.01)

(58) Field of Classification Search
  USPC .......... 73/1.79, 1.38; 702/33, 113, 116, 150, 702/142; 700/90
  See application file for complete search history.

(56) References Cited

FOREIGN PATENT DOCUMENTS

| KR | 10-2013-0016025 A | 2/2013 |
|---|---|---|
| KR | 10-1263129 B1 | 5/2013 |
| KR | 10-2014-0107062 A | 9/2014 |
| WO | 2013/191491 A1 | 12/2013 |

OTHER PUBLICATIONS

Chris Otto et al., "System Architecture of a Wireless Body Area Sensor Network for Ubiquitous Health Monitoring", Journal of Mobil Multimedia, vol. 1, No. 4, Jan. 2006, pp. 307-326.

Korean Office Action for corresponding Korean Patent Application No. 10-2015-7028930 dated Aug. 18, 2016.

International Search Report dated Aug. 1, 2016 for PCT/KR2015/010698.

SYSTEM, METHOD, AND PROGRAM FOR INITIALIZING ATTACHMENT LOCATION OF MEASUREMENT SENSOR

CROSS-REFERENCE TO RELATED APPLICATIONS

The present application is a continuation of U.S. patent application Ser. No. 15/344,601, filed on Nov. 7, 2016, which is a continuation of International Patent Application No. PCT/KR2015/010698, filed Oct. 12, 2015. The disclosure of the above-listed applications are hereby incorporated by reference herein in its entirety.

BACKGROUND

Embodiments of the inventive concept described herein relate to a system, a method, and a program for initializing an attachment location of a measurement sensor, and more particularly to a system, a method, and a program for initializing attachment locations of one or more measurement sensors attached to a body of the user.

Due to the development of electronic device and various sensor technologies, the electronic devices have been complexly equipped high-end functions, and in order to input a command of the user, the methods of inputting a command through a voice or a motion of the user without using a traditional separate interface device, such as a remote controller, a keyboard, or a mouse, have been actively developed (Korean Patent Application Publication No. 2013-0016025).

In particular, in recent years, the control technologies for driving a device by recognizing a motion of the user and extracting a user command have been actively studied as the sensor technologies have been developed.

Korean Patent Application Publication No. 2012-0000807 discloses a technology of matching an input command with various motion forms of the user, and when the user takes a specific motion, recognizing the motion and executing a corresponding driving command.

Further, the sensing technology for a body motion is used to evaluate whether a body motion of the user is proper as well as to input a command to an electronic device. For example, the sensing technology may be used to verify whether a specific motion of an athlete accurately perform a specific motion during an exercise, or to verify whether a motion of the patient is suitable for training of muscles of a body portion during a rehabilitation exercise of the rehabilitation patient.

The methods of measuring a body motion of the user include a method of measuring a change in a motion by attaching a sensor to the human body and a method of recognizing a motion by using a vision sensor. When a sensor, such as an inertia sensor, is attached to a body portion of the user to measure a motion of the user, it is necessary to set the body portion, to which the sensor is attached. That is, it is necessary to initially determine a motion of which body portion sensing data measured by the sensor corresponds to.

SUMMARY

Embodiments of the inventive concept provide a system, a method, and a program that initialize an attachment location of a measurement sensor to calculate a posture or motion of a whole body of the user by combining sensing data acquired through the measurement sensor.

Embodiments of the inventive concept also provide a system, a method, and a program that initialize a detailed point in a body unit, to which a measurement sensor is attached, to increase the measurement accuracy of a motion of the user.

In accordance with an aspect of the inventive concept, there is provided a method of determining an initial attachment location of at least one measurement sensor, the method being performed by a terminal, the method including retrieving identification information of the at least one measurement sensor selected from a user, as the terminal receives a selection input for the at least one measurement sensor attached to a particular location of a body of the user, from the user, and matching the retrieved identification information with the particular location of the body where the at least one measurement sensor is configured to be attached such that the initial attachment location of the at least one measurement sensor is determined.

In accordance with another aspect of the inventive concept, there is provided a non-transitory computer-readable recording medium in which a program for determining an initial attachment location of a measurement sensor, which is coupled to a terminal that is hardware. The program includes instructions to execute a method including retrieving identification information of the at least one measurement sensor selected from a user, as the terminal receives a selection input for at least one measurement sensor attached to a particular location of a body of the user, from the user, and matching the retrieved identification information with the particular location of the body where the at least one measurement sensor is configured to be attached such that the initial attachment location of the at least one measurement sensor is determined.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
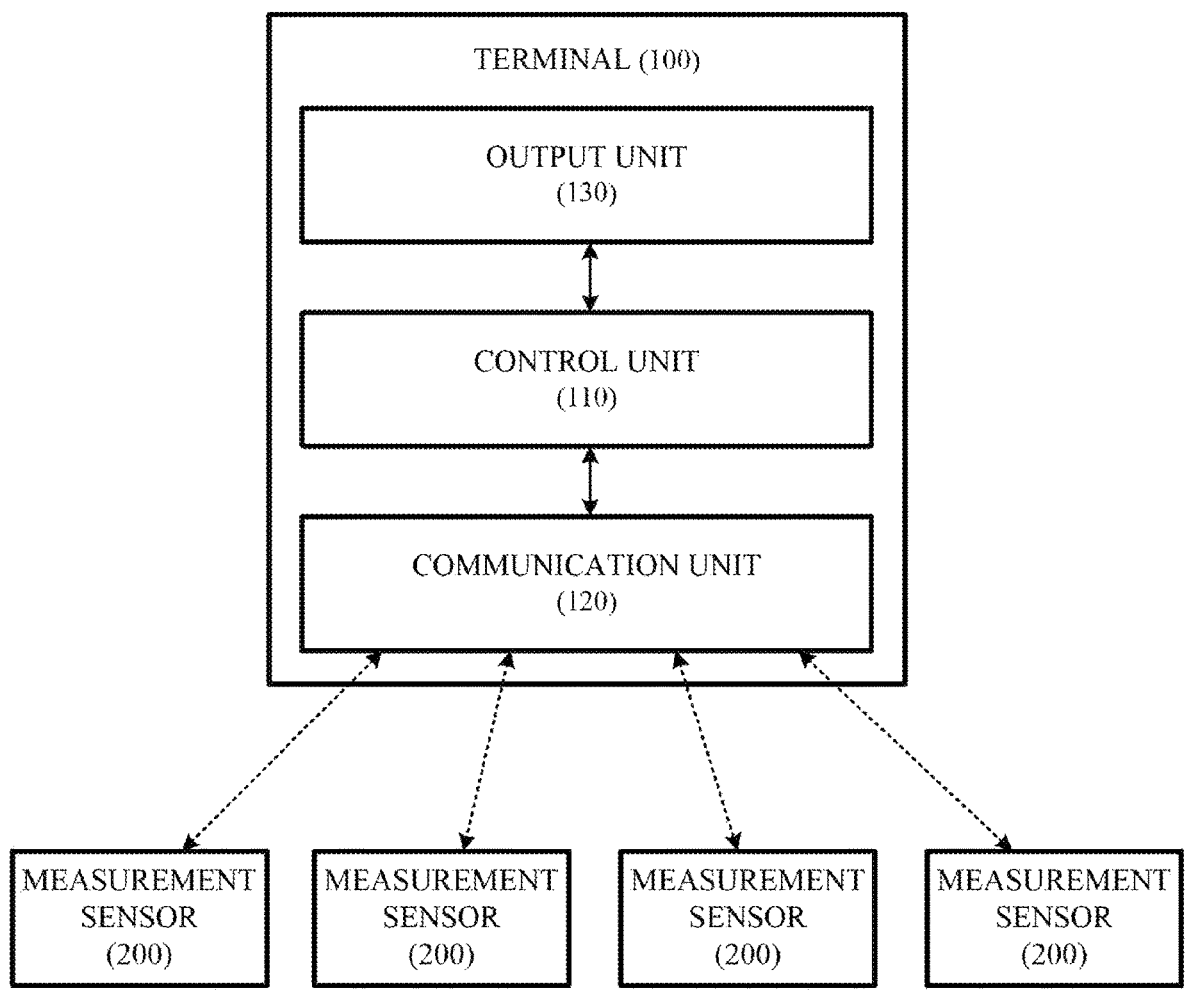
FIG. 1 is a block diagram illustrating a system for initializing an attachment location of a measurement sensor when a terminal and the measurement sensor directly perform communication according to an embodiment of the inventive concept.

Hereinafter, exemplary embodiments of the inventive concept will be described in detail with reference to the accompanying drawings. The above and other aspects, features and advantages of the invention will become apparent from the following description of the following embodiments given in conjunction with the accompanying drawings. However, the inventive concept is not limited to the embodiments disclosed below, but may be implemented in various forms. The embodiments of the inventive concept is provided to make the disclosure of the inventive concept complete and fully inform those skilled in the art to which the inventive concept pertains of the scope of the inventive concept. The same reference numerals denote the same elements throughout the specification.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The terms used herein are provided to describe the embodiments but not to limit the inventive concept. In the specification, the singular forms include plural forms unless particularly mentioned. The terms "comprises" and/or "comprising" used herein does not exclude presence or addition of one or more other elements, in addition to the aforementioned elements.

Throughout the specification, a body unit refers to a portion of the body of the user, to which a measurement sensor is attached. For example, a body unit may refer to a minimum unit of the body that may move independently. That is, the body unit may refer to a portion of the body that is not bent any more by a joint.

Throughout the specification, identification information refers to data, by which measurement sensors are distinguished. That is, the identification information refers to information that is provided in a plurality of measurement sensors having the same external appearance such that the measurement sensors may by distinguished by a terminal. For example, the identification information may correspond to addresses (that is, Mac addresses) that are given for communication.

Hereinafter, a system, a method, and a program for initializing an attachment location of a measurement sensor according to embodiments of the inventive concept will be described with reference to the accompanying drawings.

Figure 2:
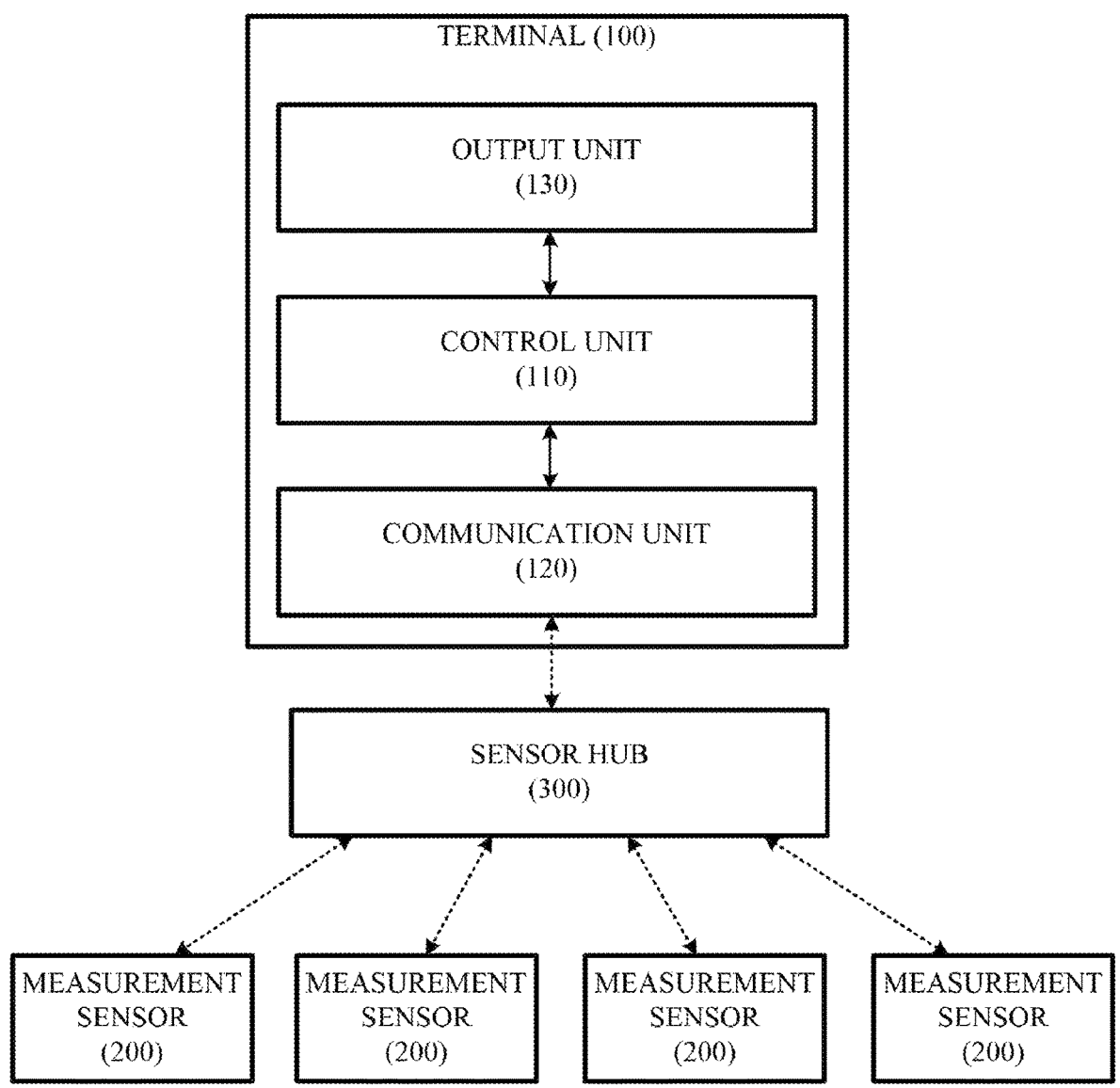
FIG. 2 is a block diagram illustrating a system for initializing an attachment location of a measurement sensor when a terminal and the measurement sensor perform communication through a sensor hub according to an embodiment of the inventive concept.

FIG. 1 is a block diagram illustrating a system for initializing an attachment location of a measurement sensor when a terminal and the measurement sensor directly perform communication according to an embodiment of the inventive concept. FIG. 2 is a block diagram illustrating a system for initializing an attachment location of a measurement sensor when a terminal and the measurement sensor perform communication through a sensor hub according to an embodiment of the inventive concept.

The system for initializing an attachment location of a measurement sensor according to an embodiment of the inventive concept may include a terminal 100 and one or more measurement sensors 200.

The terminal 100 may be classified into a mobile terminal 100 and a fixed terminal 100 according to a mobility thereof, and all types of terminals 100 that constitute the configuration may be applied. For example, a mobile terminal 100 may include a cellular phone, a personal communication service (PCS) phone, a synchronous/asynchronous international mobile telecommunication-2000 (IMT-2000) mobile terminal, a palm personal computer (PC), a personal digital assistant (PDA), a smartphone, a wireless application protocol (WAP) phone, a mobile gaming device, a tablet PC, a netbook, and a notebook, and a fixed terminal 100 may include a desktop PC and a television.

The terminal 100 includes all or some of a control unit 110, a communication unit 120, and an output unit 130. The elements of the terminal 100 are not limited to the described elements, and may further include additional elements.

The control unit 110 generally controls an overall operation of the terminal 100. For example, the control unit 110 performs data communication, image processing for reproduction of an image on a display, and control and processing related to initialization of an attachment location. Various functions that are performed by the control unit 110 will be described.

The communication unit 120 performs a function of receiving sensing data from the measurement sensor 200. Further, the communication unit 120 performs a function of delivering the received sensing data to the control unit 110. Further, the communication unit 120 may transmit an output depending on an evaluation result calculated based on the sensing data, to the measurement sensor 200.

The communication unit 120 may include a wired communication unit 120 that is connected wired to the measurement sensor 200 to receive data, or a wireless communication unit that receives sensing data from the measurement sensor 200 (or a sensor hub 300 that is connected to the measurement sensor 200) through a wireless communication scheme. The wireless communication unit may include a wireless internet module or a short range communication module.

The wireless internet module refers to a module for wireless internet connection, and may be installed inside or outside the terminal 100. The wireless internet technology may include wireless LAN (WLAN) (Wi-Fi), wireless broadband (Wibro), world interoperability for microwave access (Wimax), high speed downlink packet access (HSDPA), long term evolution (LTE), long term evolution-advanced (LTE-A).

The short range communication module refers a module for short range communication. The short range communication technology may include Bluetooth, Bluetooth low energy (BLE), Beacon, radio frequency identification (RFID), near field communication (NFC), infrared data association (IrDA), ultra-wideband (UWB), ZigBee, and NRF.

The output unit 130 performs a function of outputting information that is to be provided to the user. In some embodiments, the output unit 130 includes a display unit or a sound output unit.

The display unit performs a function of displaying (outputting) information that is processed by the terminal 100. For example, the display unit outputs a motion of the user that is generated by combining sensing data acquired by the measurement sensor 200. Further, the display unit performs a function of displaying an item which is to be requested to the user such that an attachment location of the measurement sensor 200 is initialized. For example, the terminal 100 performs a request for an input for a measurement sensor 200, attached by the user, on the display unit.

Further, in some embodiments, the display unit is coupled to a touch sensor to be implemented as a touchscreen. The display unit receives an input manipulation from the user through a touch manipulation. For example, the terminal 100 receives the input to select a specific point in a body shape of a person displayed on a screen and designate an accurate attachment location in a body unit of a specific user.

The various embodiments described herein, for example, may be implemented by a recording medium that may be read by a computer or a similar device by using software, hardware, or a combination thereof.

In some embodiments, the terminal 100 further includes a memory. The memory stores a program for an operation of the control unit 110, and stores data that is input and output or data (for example, learning data that is stored after motion data is received) generated while a motion of the body is evaluated. In some embodiments, the memory is included in the control unit 110.

In some embodiments, the memory includes at least one type of storage medium of a flash memory type, a hard disk type, a multimedia card micro type, or a card type memory (for example, an SD or XD memory), a random access memory (RAM), a static random access memory (SRAM), a read only memory (ROM), an electrically erasable programmable read only memory (EEPROM), a programmable read only memory (PROM), a magnetic memory, a magnetic disk, and an optical disk. In some embodiments, the mobile terminal 100 is operated in relation to a web storage that performs a storage function of the memory on the internet.

According to hardware implementations, the embodiments described herein are implemented by using at least one of an application specific integrated circuit (ASIC), a digital signal processor (DSP), a digital signal processing device (DSPD), a programmable logic device (PLD), a field programmable gate array (FPGA), a processor, a controller, a micro-controller, a microprocessor, and an electrical unit for performing other functions. In some cases, the embodiments described herein may be implemented by the control unit 110 itself.

According to software implementations, the embodiments such as the procedures and functions described herein are implemented by separate software modules. The software modules perform one or more functions and operations described herein.

In some embodiments, the software code is implemented by a software application that is written in a suitable program language. The software code is stored in the memory and executed by the control unit 110.

The measurement sensor 200 is attached to a specific body unit, and performs a function of acquiring sensor data on a motion of the specific body unit. For example, the measurement sensor 200 includes a fixing unit such as a band to be attached to a specific body unit of the user, and an adhesive that allows the measurement sensor 200 to be attached to and detached from the body may be provided on one surface of the measurement sensor 200 such that the measurement sensor 200 may be attached to the specific body unit.

The measurement sensor 200 includes a senor that measures a motion of the user therein. For example, the measurement sensor 200 includes an inertia sensor, a gyro sensor, or a geomagnetic sensor to acquire sensing data depending on a motion of the user.

The measurement sensor 200 performs a function of transmitting sensing data to the terminal 100 through wired/wireless communication. In some embodiments, as illustrated in FIG. 1, the measurement sensor 200 directly transmits sensing data to the terminal 100. For example, the measurement sensor 200 is connected to the terminal 100 through NRF communication without performing a pairing operation to transmit sensing data.

Further, in some embodiments, as illustrated in FIG. 2, the measurement sensor 200 transmits and receives sensing data to and from the terminal 100 through the sensor hub 300. The sensor hub 300 performs a function of receiving sensing data from one or more measurement sensors 200 and transmitting the received sensing data to the terminal 100. For example, the sensor hub 300 receives sensing data from the measurement sensor 200 through NRF communication, and may transmit the received sensing data to the terminal 100 through Bluetooth communication. Through this, only the sensor hub 300 is connected to the terminal 100 to be conveniently used, without the one or more measurement sensors 200 are connected to the terminal 100. Further, in some embodiments, the sensor hub 300 is connected to the one or more measurement sensors 200 to perform a cradle for charging.

Hereinafter, a method of initializing an attachment location of a measurement sensor 200 by a terminal 100 according to embodiments of the inventive concept will be described.

Figure 3:
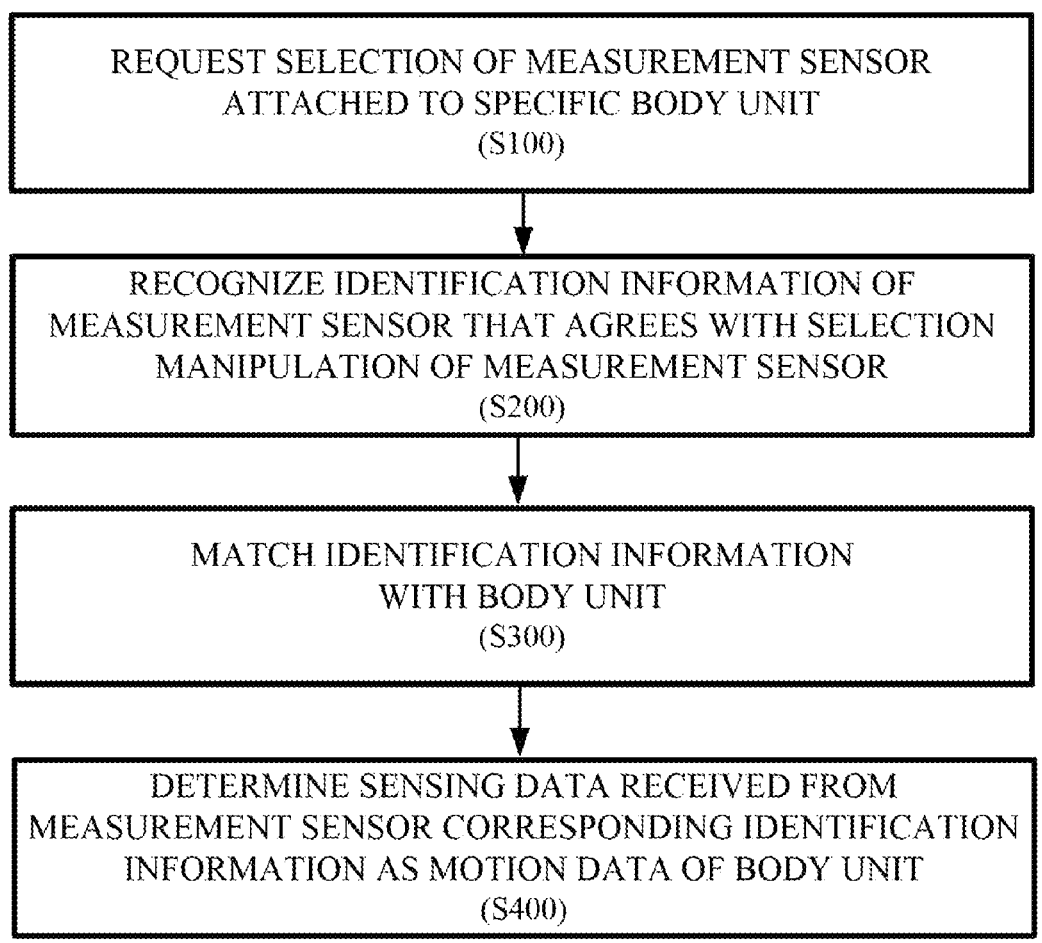
FIG. 3 is a flowchart illustrating a method of initializing an attachment location of a measurement sensor by a terminal according to an embodiment of the inventive concept.

FIG. 3 is a flowchart illustrating a method of initializing an attachment location of a measurement sensor 200 by a terminal 100 according to an embodiment of the inventive concept.

Referring to FIG. 3, a method of initializing an attachment location of a measurement sensor 200 by a terminal 100 according to an embodiment of the inventive concept includes: an operation S100 of requesting selection of a measurement sensor attached to a specific body unit; an operation S200 of recognizing identification information of a specific measurement sensor 200 that agrees with the selection manipulation of the specific measurement sensor 200; an operation S300 of matching the identification information with the body unit; and an operation S400 of determining sensing data received from the measurement sensor 200 corresponding to the identification information as motion data of the body unit. A method of initializing an attachment location of a measurement sensor 200 by a terminal 100 according to an embodiment of the inventive concept will be described in sequence.

The measurement sensors 200 are not limited to a sensor for a specific body portion but may have the same form for a generic purpose, and only identification information included in the measurement sensors 200 may be different. Accordingly, the terminal 100 has to match identification information of the attached measurement sensor 200 with the body unit to which the measurement sensor 200 is attached, to recognize an accurate posture or motion of the user.

To achieve this, first, the terminal 100 requests selection of the measurement sensor 200 attached to the specific body unit (S100). That is, the terminal 100 requests selection of a specific measurement sensor 200, which is to be attached to a specific body unit, from the plurality of measurement sensors 200 through a voice output or a screen output.

In some embodiments, the terminal 100 suggests one or more body units, to which the measurement sensors 200 need to be attached, in sequence, and requests designation or selection of a specific measurement sensor 200 which is to be attached to the suggested body unit.

Further, in some embodiments, the terminal 100 allows the user to select a specific body unit from several body unit lists displayed on a screen or may allow the user to select a point corresponding to a specific body unit from an image of a shape of a person displayed on the screen. Thereafter, the terminal 100 requests selection of a measurement sensor 200 that is to be attached to a selected body unit.

Further, in some embodiments, the terminal 100 extracts a body unit, to which a measurement sensor 200 needs to be attached, depending on a motion form requested by the user, and requests designation of the measurement sensors 200, which are to be attached to the one or more extracted body units, in sequence. For example, when the user performs a rehabilitation exercise for shoulders while wearing a measurement sensor 200, a portion of the body, a motion of which needs to be sensed, is selected during the rehabilitation exercise for shoulders because there is no need to attach a measurement sensor 200 to the lower part of the body.

In some embodiments, To achieve this, the method further include: an operation of receiving an selection input in a form of a specific exercise from the user; and an operation of extracting one or more body units, to which the measurement sensor 200 needs to be attached, based on the exercise form. First, the user selects a desired exercise form through various user inputs (for example, a touch manipulation of a touchscreen of the terminal 100 and a voice command for the terminal 100). Thereafter, the terminal 100 extracts an attachment location of the measurement sensor 200 that agrees with the exercise form selected by the user. For example, the terminal 100 matches body units followed by motions when a specific motion form is performed with an exercise form to store the result, and determine the one or more matched body units as attachment locations of the measurement sensor 200 if a specific exercise form is selected by the user.

In some embodiments, the operation S100 of requesting selection of a measurement sensor includes: when the user is requested to attach a measurement sensor 200 to a specific body unit, dividing the body unit into detailed units based on the number of the measurement sensors 200, which is required to be attached to the specific body unit. For example, if two measurement sensors 200 are attached between an elbow and a shoulder to calculate an accurate posture or motion of the user, the terminal 100 divides an area between the elbow and the shoulder, which is one body unit, into two detailed units. That is, the terminal 100 divides one body unit into 'a shoulder surrounding area and an elbow surrounding area' or 'a biceps brachii area and a triceps brachii area'. The terminal 100 requests selection or designation of a measurement sensor 200, which is to be attached for a detailed unit, to the user.

The terminal 100 recognizes identification information of a specific measurement sensor 200 that agrees with the selection manipulation of the specific measurement sensor 200 (S200). That is, the terminal 100 recognizes identification information of the specific measurement sensor 200 selected by the user. The terminal 100 may directly receive a selection manipulation from the measurement sensor 200, and recognize identification information of the measurement sensor 200, the selection manipulation of which is received. In some embodiments, to achieve this, the operation S200 of recognizing the identification information includes: an operation of receiving a selection manipulation from the specific measurement sensor 200; and an operation of recognizing identification information of the measurement sensor 200, the selection manipulation of which is received.

In some embodiments, when the measurement sensor 200 includes a button, the selection manipulation may be a manipulation of a button that is attached to the measurement sensor 200. That is, the user manipulates a button of the measurement sensor 200, which is to be attached to a body unit requested by the terminal 100, and the terminal 100 acquires a wireless signal from the measurement sensor 200, the button of which has been manipulated. Thereafter, the terminal 100 recognize identification information of the measurement sensor 200, the button of which has been manipulated. The terminal 100 directly receives and recognizes identification information from the measurement sensor 200, and searches an identification information list for the identification information corresponding to the measurement sensor 200, which transmitted a wireless signal, to recognize the found identification information.

Further, in some embodiments, the selection manipulation corresponds to a specific selection manipulation operation that is input to the measurement sensor 200. That is, the terminal 100 requests a selection manipulation operation input for the specific measurement sensor 200 to the user, and recognizes the identification information of the measurement sensor 200, a selection manipulation of which is input. For example, the terminal 100 requests the user to perform a specific operation, for example, of shaking or turning the measurement sensor 200 a specific number of times or more as a selection manipulation operation. The terminal 100 recognizes a measurement sensor 200, by which a specific selection manipulation operation is sensed, as the measurement sensor 200 attached to the specific body unit requested by the terminal 100 to recognize identification information. The terminal 100 receives a wireless communication signal only from a measurement sensor 200, to which a specific selection manipulation is input, to recognize the selected measurement sensor 200, and may receive a wireless signal (for example, an NRF signal) from all the measurement sensors 200 continuously or periodically to recognize a measurement sensor that is selected by distinguishing the measurement sensors in a stopped state (that is, a state in which a selection manipulation is not input) and the measurement sensor, to which a selection manipulation is input.

Further, in some embodiments, as illustrated in FIG. 2, when the terminal 100 is connected to the measurement sensor 200 through the sensor hub 300, the terminal 100 receive identification information of the specific measurement sensor 200, to which a selection manipulation has been input, from the sensor hub 300.

In some embodiments, a measurement sensor 200 is selected by manipulating buttons (for example, the sensor hub 300 includes connectors that connect a plurality of measurement sensors 200, respectively, and the buttons are included in areas that are adjacent to the connectors) corresponding to the measurement sensors 200, and the sensor hub 300 transmits the identification information of the selected measurement sensor 200 to the terminal 100 (for example, the sensor hub 300 recognizes the identification information of the measurement sensor 200 connected to the connector corresponding to the manipulated button to transmit the recognized identification information to the terminal 100).

Further, in some embodiments, when the selection manipulation corresponds to a selection manipulation operation that is input to the measurement sensor 200, the sensor hub 300 receives a signal from the measurement sensor 200, to which a specific manipulation operation (for example, shaking, overturning, or turning), and recognizes identification information of the measurement sensor 200, which received the signal, to transmit the recognized identification information to the terminal 100.

The terminal 100 matches the identification information with the body unit (S300). That is, the terminal 100 matches the measurement sensor 200 selected through the selection manipulation with a specific body unit. The terminal 100 sets a reference point of data that is measured by the measurement sensors 200, by matching the specific measurement sensor 200 with the body unit.

The terminal 100 determines sensing data received from the measurement sensor 200 corresponding to the identification information as motion data of the body unit (S400).

Further, in some embodiments, the method further includes: an operation of, when one or more measurement sensors 200 are attached to the body of the user, requesting the user to perform a specific motion or posture by the terminal 100; an operation of, as the motion or posture is performed, combining the motion or posture with the corresponding body unit to generate whole body motion or whole posture information; and a normal motion determining operation of determining whether the whole body motion or whole body posture corresponds to a normal body motion. If a measurement sensor 200 is attached to the body of the user differently from the matching relationship between the measurement sensor 200 and the body unit, which was performed by the terminal 100, an error may be generated in the process of matching the identification information of the measurement sensor 200 and the body unit. Accordingly, the terminal 100 requests the user to perform a specific reference posture or reference motion, and determines whether the generated whole body posture or motion agrees with a general posture or motion of a person.

In detail of the embodiment, when the user is requested to perform a specific posture, the operation of determining the normal motion includes: an operation of setting sensing ranges of body units that agree with the posture; and determining whether the sensing data received from the measurement sensors 200 attached to the body units is included in the sensing range. That is, because a sensing range is expected for the body unit when the user is requested to take a specific posture, it is determined whether the sensing data (for example, an inclination that is made with reference to the bottom surface) that is actually measured when a specific reference posture of the user is performed is included in an expected range, for the body unit, to verify whether the measurement sensor 200 is properly attached.

Further, in some embodiments, in the operation of determining the normal motion, when the user is requested to perform a specific operation (that is, a motion), it is verified whether the measurement sensors 200 are properly attached to the corresponding body units, by comparing a change in a sensing value that is expected for the body portion and a change in a sensing value that is actually measured.

Further, in some embodiments, when the whole body motion or whole body posture does not correspond to a normal motion, the method further includes an operation of determining a measurement sensor 200 attached to an erroneous body unit that does not correspond to the normal motion. For example, when a first measurement sensor 200 designated to be attached to a wrist and a second measurement sensor 200 designated to be attached to a thigh are replaced by each other, the first measurement sensor 200 is in a vertical state differently from a horizontal state that is an expected inclination state and the second measurement sensor 200 is in a horizontal state differently from an expected vertical state in a specific reference posture (for example, a posture in which the user stands while widening the arms), so that the terminal 100 recognizes that the first measurement sensor 200 and the second measurement sensor 200 are attached to wrong locations. Further, for example, when a first measurement sensor 200 designated to be attached to a wrist and a second measurement sensor 200 designated to be attached to a thigh are replaced by each other, an angle change range of the second measurement sensor 200 is changed to be larger than an expected range for the angle change range by not less than a specific ratio in a specific reference operation (for example, the user jumps while widening the arms), so that the terminal 100 recognizes an erroneous attachment of the second measurement sensor 200.

Further, in some embodiments, the method further includes: an operation of calculating a pair of erroneous body units, the corresponding measurement sensors of which are required to be exchanged; and an operation of requesting the user to exchange the locations of the measurement sensors attached to the pair of erroneous body units. That is, the pair of erroneous body units, the locations of which are required to be replaced, is calculated, and the user is requested to replace the locations of the measurement sensors attached to the erroneous body units. The erroneous body unit refers to a body portion, to which it is determined that the measurement sensor 200 matched by the terminal 100 is not properly attached. First, the terminal 100 calculates a pair of erroneous body units, the locations of which are required to be replaced by each other (that is, match or connect the erroneous body units, the locations of which are to be replaced by each other). For example, when the sensing data of the body units, to which the measurement sensors 200 are considered to be wrongly attached, are replaced by each other, a pair of erroneous body units that are to be replaced by each other is calculated by determining the sensing data corresponds to a normal motion. Thereafter, the terminal 100 requests the user to replace the locations of the measurement sensors attached to the pair of erroneous body units. That is, the terminal 100 guides two body units, to which the current measurement units 200 are attached, to the user and requests a change of the attachment locations.

Further, in some embodiments, the method further includes: an operation of calculating a pair of erroneous body units, the corresponding measurement sensors of which are required to be replaced; and an operation of exchanging the locations of the measurement sensors connected to the pair of erroneous body units. That is, the terminal recognizes a pair of erroneous body units, to which the user wrongly attached the measurement sensors (that is, two body units by which a motion of the user may be determined to be normal if the attachment locations are changed), and exchange the identification information matched with the erroneous body units. Through this, the terminal automatically removes the erroneous body units without replacing a separate measurement sensor.

Further, in some embodiments, the sensing data values are different depending on the detailed points, to which the measurement sensors 200 are attached in the body units. For example, when the measurement sensor 200 is attached to an arm, the sensing data values may be different when the measurement sensor 200 is attached to a biceps brachii and a triceps brachii. Further, when the measurement sensor 200 is attached to an arm, the sensing data values may be different when the measurement sensor 200 is attached close to a shoulder and close to an elbow. (For example, when an operation of rotating an arm is performed, the measurement sensor 200 moves faster when the measurement sensor 200 is attached to the vicinity of an elbow rather than when the measurement sensor 200 is attached to the vicinity of a shoulder and may move in a larger range.) Accordingly, in order to accurately recognize a posture or an operation (motion) of the user, it is necessary to set a detailed point of the body unit.

The method of setting a detailed point in a body unit further includes: an operation of requesting the user to take one or more postures; an operation of, when the posture is performed, receiving sensing data from the measurement sensor 200; and an operation of calculating a detailed point of the body unit, to which the measurement sensor 200 is attached by the user, based on a value of the sensing data. That is, the terminal requests the user to take one or more reference postures by displaying one or more reference postures on a screen in sequence or simultaneously, and calculates body units based on the sensing data depending on the one or more reference postures.

Further, a method of setting a detailed point in a body unit according to another embodiment may include: an operation of requesting designation of a detailed point of the body unit through a touch screen by the terminal 100; and an operation of receiving an input for designating the detailed point of the body unit, which is displayed on the touch screen, from the user. Because a specific body unit and a measurement sensor of specific identification information are matched with each other, the terminal 100 may match a detailed point of the specific body unit and the measurement sensor 200 if only the detailed point of the body unit is designated. Accordingly, the terminal 100 provides a whole body image on a touch screen, or provides enlarged images of the body units in sequence and receives a touch manipulation at a point on a screen corresponding to a detailed point.

Through this, the terminal may accurately calculate a posture or motion taken by the user, by accurately setting an attachment location of the measurement sensor 200.

Further, in some embodiments, different reference selection manipulation operations may be set for the body units in the selection requesting operation S100, and the measurement sensor 200 is matched with the body unit by comparing a selection manipulation operation that is input by the measurement sensor 200 and the reference selection manipulation operation in the identification information matching operation S300. That is, when a specific manipulation operation is input to the measurement sensor while being taken as a selection manipulation, the terminal 100 matches the measurement sensor 200, to which an input selection manipulation operation is input, and a body unit to which a reference selection manipulation operation that coincides with an input selection manipulation operation, by differently setting the reference selection manipulation operations for respective body units.

The method of initializing an attachment location of a measurement sensor 200 according to an embodiment of the inventive concept may be coupled to a computer that is a piece of hardware to be implemented by a program (or an application) and stored in a medium.

The program may include a code that is coded in a computer language, such as C, C++, JAVA, or a machine language, by which a processor of the computer may be read through a device interface of the computer, to execute the methods implemented by a program after the computer reads the program. The code may include a functional code related to a function that defines necessary functions that execute the methods, and the functions may include an execution procedure related control code necessary to execute the functions in its procedures by the processor of the computer. Further, the code may further include additional information that is necessary to execute the functions by the processor of the computer or a memory reference related code on at which location (address) of an internal or external memory of the computer should be referenced by the media. Further, when the processor of the computer is required to perform communication with another computer or server in a remote site to allow the processor of the computer to execute the functions, the code may further include a communication related code on how the processor of the computer executes communication with another computer or server or which information or medium should be transmitted and received during communication by using a communication module of the computer.

The stored medium refers not to a medium, such as a register, a cash, or a memory, which stores data for a short time but to a medium that stores data semi-permanently and is read by a device. In detail, an example, of the stored medium may include a ROM, a RAM, a CD-ROM, a magnetic tape, a floppy disk, and an optical data storage device, but the inventive concept is not limited thereto. That is, the program may be stored in various recording media on various servers, which the computer may access, or in various recording media on the computer of the user. Further, the media may be dispersed in a computer system connected to the medium through a network, and codes that may be read by the computer in a dispersion manner may be stored.

The inventive concept has the following effects.

First, because the attachment locations of the plurality of measurement sensors are initialized, the terminal may accurately calculate a posture or motion of the user.

Second, erroneous attachments of the measurement sensors may be identified by determining a posture or motion generated by coupling sensing data of the measurement sensors matched to body portions corresponds to a normal posture or motion of a person. Through this, because a matching relationship between the attached body unit and the measurement sensors may be double-checked, the attachment locations of the measurement sensors may be accurately initialized.

Third, because a detailed point in a specific body unit, to which the measurement sensor is attached, may be determined, the terminal may accurately calculate a posture or motion of the user.

Although the exemplary embodiments of the inventive concept have been described with reference to the accompanying drawings, it will be understood by those skilled in the art to which the inventive concept pertains that the inventive concept can be carried out in other detailed forms without changing the technical spirits and essential features thereof. Therefore, the above-described embodiments are exemplary in all aspects, and should be construed not to be restrictive.

What is claimed is:

1. A method of determining an initial attachment location of at least one measurement sensor, the method being performed by a terminal, the method comprising:
    retrieving, by the terminal, identification information of the at least one measurement sensor, as the terminal receives a selection input from a user, wherein the at least one measurement sensor is configured to be attached to a particular location of a body of the user and is selected according to the selection input, among a plurality of measurement sensors; and
    matching, by the terminal, the retrieved identification information with the particular location of the body where the at least one measurement sensor is configured to be attached such that the initial attachment location of the at least one measurement sensor is determined,
    wherein the retrieving the identification information comprises:
    receiving, by the terminal, from a sensor hub, the identification information, which corresponds to the selection input, and
    wherein the sensor hub is connected to a plurality of measurement sensors and the terminal through wireless communication, recognizes the at least one measurement sensor among the plurality of measurement sensors based on the selection input received at the terminal, retrieves the identification information of the at least one measurement sensor corresponding to the selection input, and transmit the retrieved identification information to the terminal.

2. The method of claim 1, further comprising:
when the at least one measurement sensor is attached to the body of the user,
acquiring, by the terminal, sensing data received from the at least one measurement sensor corresponding to the identification information as motion data of the particular location of the body of the user, based on the determined initial attachment location.

3. The method of claim 1, wherein the retrieving the identification information comprises:
receiving, by the terminal, the selection input from the user, via the at least one measurement sensor; and
retrieving, by the terminal, the identification information based on the selection input received via the at least one measurement sensor.

4. The method of claim 1, wherein the matching comprises:
when a plurality of measurement sensors needs to be attached to a specific location of the body, dividing, by the terminal, the specific location into a plurality of detailed locations, based on the number of the plurality of measurement sensors.

5. The method of claim 1, wherein the retrieving the identification information comprising:
outputting, by the terminal, a message indicating a plurality of measurement sensors that needs to be attached to the body of the user; and
receiving, by the terminal, the selection input.

6. The method of claim 1, wherein the retrieving the identification information comprising:
outputting, by the terminal, a message indicating a plurality of locations of the body, to which a plurality of measurement sensors needs to be attached;
outputting, by the terminal, a message indicating a plurality of measurement sensors that needs to be attached to the indicated plurality of locations of body; and
receiving, by the terminal, the selection input.

7. The method of claim 1, wherein the retrieving the identification information comprising:
outputting, by the terminal, a message indicating a plurality of locations of the body;
receiving, by the terminal, a selection input for a location of the body;
outputting, by the terminal, a message indicating a plurality of measurement sensors configured to be attached to the location of the selection input; and
receiving, by the terminal, the selection input for the at least one measurement sensor.

8. The method of claim 1, wherein the retrieving the identification information comprising:
receiving, by the terminal, information on a type of exercise to be performed by the user;
outputting, by the terminal, a message indicating a plurality of locations of the body, which correspond to the type of exercise to be performed by the user;
receiving, by the terminal, a selection input for a location of the body;
outputting, by the terminal, a message indicating a plurality of measurement sensors configured to be attached to the location of the selection input; and
receiving, by the terminal, the selection input for the at least one measurement sensor.

9. The method of claim 1, wherein the retrieving the identification information further includes:
sequentially presenting, by the terminal, body units requiring attachment of the measurement sensor; and
receiving, by the terminal, the selection input of a particular measurement sensor to be attached to the presented body units.

10. The method of claim 1, wherein the selection input includes:
an input to select a particular body unit from a list of several body units displayed on a screen of the terminal.

11. The method of claim 1, wherein the selection input includes:
an input to select a point corresponding to a particular body unit in a human shape image displayed on a screen of the terminal.

12. A method of determining an initial attachment location of at least one measurement sensor, the method being performed by a terminal, the method comprising:
retrieving, by the terminal, identification information of the at least one measurement sensor, as the terminal receives a selection input from a user, wherein the at least one measurement sensor is configured to be attached to a particular location of a body of the user and is selected according to the selection input, among a plurality of measurement sensors; and
matching, by the terminal, the retrieved identification information with the particular location of the body where the at least one measurement sensor is configured to be attached such that the initial attachment location of the at least one measurement sensor is determined,
wherein the selection input includes:
setting different reference selection operations for different locations of the body, and
wherein the matching the retrieved identification information comprises:
comparing, by the terminal, a selection operation of the selection input received at the at least one measurement sensor and the reference selection manipulation operations, and matching, by the terminal, the at least one measurement sensor with the particular location of the body based on a result of the comparing.

13. A non-transitory computer-readable recording medium in which a program is stored, wherein the program includes instructions for determining an initial attachment location of a measurement sensor that is coupled to a terminal that is hardware, and the instructions are configured to execute a method comprising:
retrieving, by the terminal, identification information of the at least one measurement sensor, as the terminal receives a selection input from a user, wherein the at least one measurement sensor is configured to be attached to a particular location of a body of the user and is selected according to the selection input, among a plurality of measurement sensors; and
matching, by the terminal, the retrieved identification information with the particular location of the body where the at least one measurement sensor is configured to be attached such that the initial attachment location of the at least one measurement sensor is determined,
wherein the retrieving the identification information comprises:

receiving, by the terminal, from a sensor hub, the identification information, which corresponds to the selection input, and wherein the sensor hub is connected to a plurality of measurement sensors and the terminal through wireless communication, recognizes the at least one measurement sensor among the plurality of measurement sensors based on the selection input received at the terminal, retrieves the identification information of the at least one measurement sensor corresponding to the selection input, and transmit the retrieved identification information to the terminal.

\* \* \* \* \*